US011132566B1

(12) United States Patent
Cherala et al.

(10) Patent No.: US 11,132,566 B1
(45) Date of Patent: *Sep. 28, 2021

(54) BLOOD VESSEL IMAGE AUTHENTICATION

(71) Applicant: Wells Fargo Bank, N.A., San Francisco, CA (US)

(72) Inventors: Saipavan K. Cherala, Hyderabad (IN); Rameshchandra Bhaskar Ketharaju, Hyderabad (IN)

(73) Assignee: Wells Fargo Bank, N.A., San Francisco, CA (US)

( * ) Notice: Subject to any disclaimer, the term of this patent is extended or adjusted under 35 U.S.C. 154(b) by 16 days.

This patent is subject to a terminal disclaimer.

(21) Appl. No.: 16/705,939

(22) Filed: Dec. 6, 2019

Related U.S. Application Data

(63) Continuation of application No. 15/823,725, filed on Nov. 28, 2017, now Pat. No. 10,515,281.

(60) Provisional application No. 62/440,145, filed on Dec. 29, 2016.

(51) Int. Cl.
| | |
|---|---|
| *G06K 9/00* | (2006.01) |
| *G06K 9/62* | (2006.01) |
| *A61B 5/1171* | (2016.01) |
| *A61B 5/024* | (2006.01) |
| *A61B 5/026* | (2006.01) |

(52) U.S. Cl.
CPC ........ *G06K 9/00885* (2013.01); *A61B 5/1171* (2016.02); *G06K 9/6202* (2013.01); *A61B 5/0261* (2013.01); *A61B 5/02444* (2013.01); *G06K 2009/00932* (2013.01)

(58) Field of Classification Search
CPC ............. G06K 9/00885; G06K 9/6202; G06K 2009/00932; A61B 5/1171; A61B 5/0261; A61B 5/02444
See application file for complete search history.

(56) References Cited

U.S. PATENT DOCUMENTS

| | | | |
|---|---|---|---|
| 5,640,468 | A | 6/1997 | Hsu |
| 6,370,262 | B1 | 4/2002 | Kawabata |
| 8,494,240 | B2 | 7/2013 | Milstein et al. |
| 8,971,637 | B1 | 3/2015 | Rivard |
| 9,626,768 | B2 | 4/2017 | Tumanov et al. |
| 10,331,291 | B1 | 6/2019 | Poder et al. |
| 10,515,281 | B1 | 12/2019 | Cherala et al. |
| 2001/0036297 | A1 | 11/2001 | Ikegami et al. |
| 2004/0004559 | A1 | 1/2004 | Rast |
| 2005/0185827 | A1 | 8/2005 | Kono et al. |
| 2006/0023919 | A1 | 2/2006 | Okamura et al. |
| 2006/0078170 | A1 | 4/2006 | Kamata et al. |
| 2006/0080547 | A1 | 4/2006 | Higashiura et al. |
| 2006/0228004 | A1 | 10/2006 | Sato et al. |

(Continued)

*Primary Examiner* — John B Strege
(74) *Attorney, Agent, or Firm* — Womble Bond Dickinson (US) LLP

(57) ABSTRACT

The innovation discloses systems and methods of authenticating users using vein or blood vessel characteristics. The innovation retrieves, based on an authentication request, an authentication image associated with a user. The authentication image comprises a first predetermined point and a second predetermined point. The innovation projects the authentication image onto a body part of the user and reads a blood vessel from the body part. The user orients the blood vessel such that it corresponds to the predetermined points in the projected authentication image. The user is authenticated when the blood vessel appears to connect the predetermined points in the direction of the blood flow.

20 Claims, 8 Drawing Sheets

(56) References Cited

U.S. PATENT DOCUMENTS

| | | |
|---|---|---|
| 2008/0183707 A1 | 7/2008 | Asano |
| 2008/0187182 A1 | 8/2008 | Abe |
| 2008/0247607 A1 | 10/2008 | Amano |
| 2009/0147998 A1 | 6/2009 | Yamaguchi et al. |
| 2009/0175505 A1 | 7/2009 | Muquit et al. |
| 2010/0135531 A1 | 6/2010 | Abe et al. |
| 2010/0315431 A1 | 12/2010 | Smith et al. |
| 2011/0029635 A1 | 2/2011 | Shkurko et al. |
| 2012/0036016 A1 | 2/2012 | Hoffberg et al. |
| 2012/0038671 A1 | 2/2012 | Min et al. |
| 2014/0016830 A1 | 1/2014 | Wang et al. |
| 2014/0294250 A1 | 10/2014 | Aoki |
| 2014/0340570 A1 | 11/2014 | Meyers et al. |
| 2015/0261991 A1 | 9/2015 | Takiguchi |
| 2015/0269760 A1 | 9/2015 | Murakami et al. |
| 2016/0004917 A1 | 1/2016 | Yoshida |
| 2016/0005154 A1 | 1/2016 | Meyers et al. |
| 2016/0171280 A1 | 6/2016 | Han et al. |
| 2016/0188860 A1 | 6/2016 | Lee et al. |
| 2016/0270656 A1 | 9/2016 | Samec et al. |
| 2016/0350503 A1 | 12/2016 | Jun et al. |
| 2017/0123492 A1 | 5/2017 | Marggraff et al. |

BLOOD VESSEL IMAGE AUTHENTICATION

CROSS-REFERENCE TO RELATED APPLICATION

This application is a continuation of U.S. patent application Ser. No. 15/823,725, filed Nov. 28, 2017, and entitled "BLOOD VESSEL IMAGE AUTHENTICATION," which claims the benefit of U.S. Provisional Patent Application No. 62/440,145, filed Dec. 29, 2016, and entitled "BLOOD VESSEL IMAGE AUTHENTICATION." The entireties of above-noted applications are incorporated by reference herein.

BACKGROUND

Authenticating users is an important process for many businesses. Authentication is sometimes reliant on a simple username/password combination that must be memorized by the user and stored by an authenticating entity. Passwords are easily forgotten, guessed, or otherwise compromised. In some instance, more complex authentication protocols have been instituted, such as two-step authentication.

Most often in two-step authentication, the authenticating entity may require a physical device such as a mobile device, tablet, or dongle to complete authentication. Such devices can be misplaced, damaged, or unavailable. Similarly, oftentimes cellular service is unavailable thereby rendering two- or dual-factor authentication inoperable. Further, these additional devices may require extra expense by the user in terms of hardware, data plans or the like.

BRIEF SUMMARY OF THE DESCRIPTION

The following presents a simplified summary of the innovation in order to provide a basic understanding of some aspects of the innovation. This summary is not an extensive overview of the innovation. It is not intended to identify key/critical elements of the innovation or to delineate the scope of the innovation. Its sole purpose is to present some concepts of the innovation in a simplified form as a prelude to the more detailed description that is presented later.

The innovation disclosed and claimed herein, in one aspect thereof, comprises systems and methods of authenticating users. The authentication can include retrieving an authentication image associated with a user, the authentication image comprises a first predetermined point and a second predetermined point. The authentication further includes projecting the authentication image onto a body part of the user, whereby the body part of the user comprises a blood vessel. The authentication includes capturing and reading blood vessel data from the body part of the user on which the authentication image is projected and comparing the blood vessel data with the first predetermined point and the second predetermined point. The authentication includes determining the blood vessel connects the first predetermined point and the second predetermined point based on the comparison; and authenticating the user based on the determination.

A system of the innovation can include an image database that comprises a set of images that include an authentication image associated with a user. The system can include a projection component that overlays the authentication image onto a body part of the user, the body part of the user containing a blood vessel and a biometric scanner that reads blood vessel data from a blood vessel on which the authentication image is overlaid. An authentication component of the system verifies an identity of the user based on the blood vessel data in relation to the authentication image overlaid onto the body part of the user.

In aspects, the subject innovation provides substantial benefits in terms of authentication and transactional security. One advantage resides in a more secure knowledge of the identity of a user. Another advantage resides in the lack of need for a password or physical device carried by a user.

To the accomplishment of the foregoing and related ends, certain illustrative aspects of the innovation are described herein in connection with the following description and the annexed drawings. These aspects are indicative, however, of but a few of the various ways in which the principles of the innovation can be employed and the subject innovation is intended to include all such aspects and their equivalents. Other advantages and novel features of the innovation will become apparent from the following detailed description of the innovation when considered in conjunction with the drawings.

BRIEF DESCRIPTION OF THE DRAWINGS

Aspects of the disclosure are understood from the following detailed description when read with the accompanying drawings. It will be appreciated that elements, structures, etc. of the drawings are not necessarily drawn to scale. Accordingly, the dimensions of the same may be arbitrarily increased or reduced for clarity of discussion, for example.

DETAILED DESCRIPTION

Figure 1:
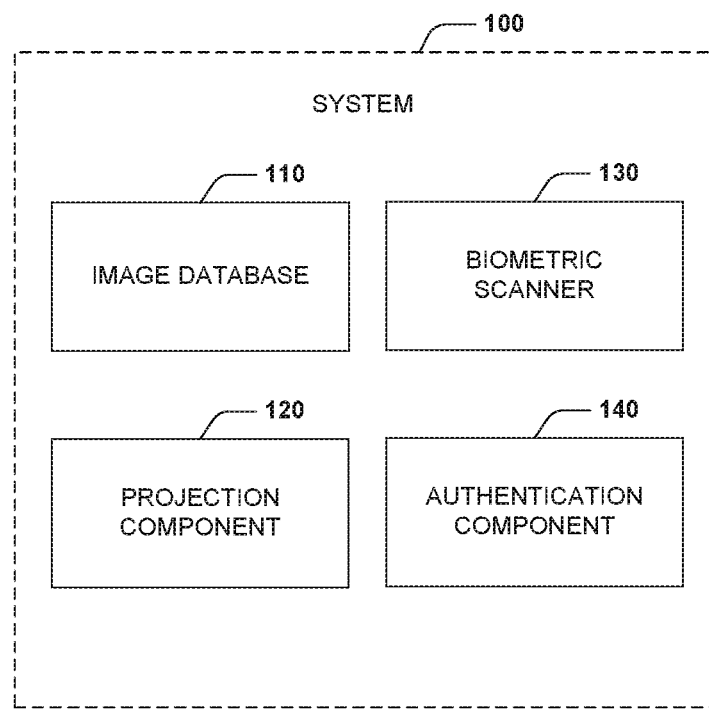
FIG. 1 illustrates an example component diagram of a system of the innovation.

The innovation is now described with reference to the drawings, wherein like reference numerals are used to refer to like elements throughout. In the following description, for purposes of explanation, numerous specific details are set forth in order to provide a thorough understanding of the subject innovation. It may be evident, however, that the innovation can be practiced without these specific details. In other instances, well-known structures and devices are shown in block diagram form in order to facilitate describing the innovation.

As used in this application, the terms "component", "module," "system", "interface", and the like are generally intended to refer to a computer-related entity, either hardware, a combination of hardware and software, software, or software in execution. For example, a component may be, but is not limited to being, a process running on a processor, a processor, an object, an executable, a thread of execution, a program, or a computer. By way of illustration, both an application running on a controller and the controller can be a component. One or more components residing within a process or thread of execution and a component may be localized on one computer or distributed between two or more computers.

Furthermore, the claimed subject matter can be implemented as a method, apparatus, or article of manufacture using standard programming or engineering techniques to produce software, firmware, hardware, or any combination thereof to control a computer to implement the disclosed subject matter. The term "article of manufacture" as used herein is intended to encompass a computer program accessible from any computer-readable device, carrier, or media. Of course, many modifications may be made to this configuration without departing from the scope or spirit of the claimed subject matter.

FIG. 1 illustrates a system 100 for authenticating a user. For instance, the authentication can be to provide access to a user account, secured data, device, network, and/or the like. For example, the system 100 can authenticate a user when a user requests to complete a financial transaction. The system 100 includes an image database 110 that can be configured to store images used for authenticating the user. An authentication image can be associated with a user during a registration described in further detail below.

The authentication image is provided when a user requests to be authenticated. The image database 110 provides authentication images associated with a user or set of users. For example, when a user attempts to withdraw cash from an automated teller machine (ATM), the user selects the authentication image that is associated with the user. In some embodiments, the images can be stock images from a third party database. In other embodiments, the images can be uploaded or selected by a user. In other embodiments, an image can be randomly selected or predetermined for a user by the system 100 or hosting entity as appropriate. While specific methodologies of image selection are described herein, it is to be understood that most any mechanism can be employed without departing from the spirit and scope of the innovation described and claimed herein.

The authentication image can be analyzed or otherwise processed to identify authentication data. The authentication data can include defined endpoints, e.g. locations or specific pixels within the authentication image. The endpoints can be tagged for association with a blood vessel (e.g. an artery or a vein) that is within a body part of a user, e.g., the palm/back of a hand or a forearm. Upon registration or subsequent authentication, information related to the blood vessel association to the endpoints can be stored within the image and/or in the image database 110.

In operation, the blood vessel and endpoints association can be determined by the system 100 or can be user designated during registration. For example, a user may select an image of a constellation of stars. Points within the image can be generated to correlate to two or more stars of the constellation. The points can be associated with a blood vessel that appears to connect the two points when the image is projected onto a user as described in greater detail below.

The system 100 includes a projection component 120. The projection component 120 receives an authentication image from the image database 110. The projection component 120 can render the authentication image onto substrates, such as skin, placed in proximity to the projection component 120. The projection component 120 casts the authentication image such that the authentication image is displayed onto a designated area of the user's skin. For example, the projection component 120 renders the authentication image onto the back of a user's hand when the user places the hand in front of the projection component 120. The designated area can be a default selection from an authenticating entity or can be designated by the user during the registration. In some embodiments, the user is directed to place their hand a designated distance away from the projection component 120.

While specific projection onto a user's body part is described, it is to be understood that most any mechanism that enables an image to be associated with a vein or blood vessel pattern or length is contemplated and to be included within the scope of the subject disclosure and claims appended hereto. For instance, pressing one's hand onto a tablet or device screen to effect the authentication comparison is understood to be included within the innovation described herein. This and other examples of similar association/vein association are to be included within the specification.

The system 100 includes a biometric scanner 130. In some embodiments, the biometric scanner 130 can operate in conjunction with projection component 120. In particular, the biometric scanner 130 can detect and observe blood vessels of a user. The biometric scanner 130 can collect data (patterns, size, depth, shape, etc.) about the blood vessel(s) of a user. Moreover, the biometric scanner 130 can read blood vessel patterns, blood flow direction, blood vessel diameter, blood vessel dilation, blood vessel location, pulse, and/or the like. The biometric scanner 130 reads the blood vessel data in association with the authentication image that is projected on the designated area of the user. In some embodiments, the biometric scanner 130 matches blood vessel data to recorded blood vessel data. In other embodiments, the biometric scanner checks the blood vessel for a pulse before authentication to rule out potential fraud.

The system 100 includes an authentication component 140. The authentication component 140 confirms the identity of a user. The authentication component 140 receives data from the projection component 120 and the biometric scanner 130. Based on at least a subset of the received data, the authentication component 140 can be configured to track a blood vessel in the designated area of the user in relation to the authentication image projected onto the designated area. The authentication component 140 can compare blood vessel location data to the authentication data within the authentication image.

In some embodiments, the authentication component 140 determines that the blood vessel connects two (or more) endpoints in the authentication image when projected onto the designated area of the user. The authentication component 140 can authenticate a user after determining the blood vessel in a designated area of a user connects two or more points in a projected authentication image associated with the user. In some embodiments, the blood vessel tracks a distinct path, recorded during registration, from a start point to an end point within the authentication image. This provides additional security in determining the same blood vessel is used for authentication with the authentication image.

The level of scrutiny and exactness of the match for authentication can correspond to most any factors including, but not limited to, user risk tolerance, data sensitivity, transaction amounts, location or the like. For instance, if a user is making a large withdrawal from an ATM, the exactness may require a higher level of scrutiny than if a very nominal transaction amount. The thresholds can be user-defined, entity-defined, account-owner defined, and/or the like.

In some embodiments, the authentication component 140 receives blood flow direction data from the biometric scanner 130. The authentication component 140 receives a start point and an end point within the authentication image from which the blood flows. The authentication component 140 authenticates the user upon determining that blood in the blood vessel flows in the correct orientation from the start point to the end point in the projected authentication image. In other embodiments, the blood vessel orientation and/or blood flow direction can be used to indicate a status of the user. In particular, a wrong orientation, wrong blood vessel, and/or wrong blood flow direction can be purposely presented by the user to the biometric scanner 130 to indicate distress and/or a state of threat. For example, the user could connect the start point and end point in the reverse direction or replace a vein with an artery (flow of blood direction would change in the opposite direction) indicating a distress call for help.

Figure 2:
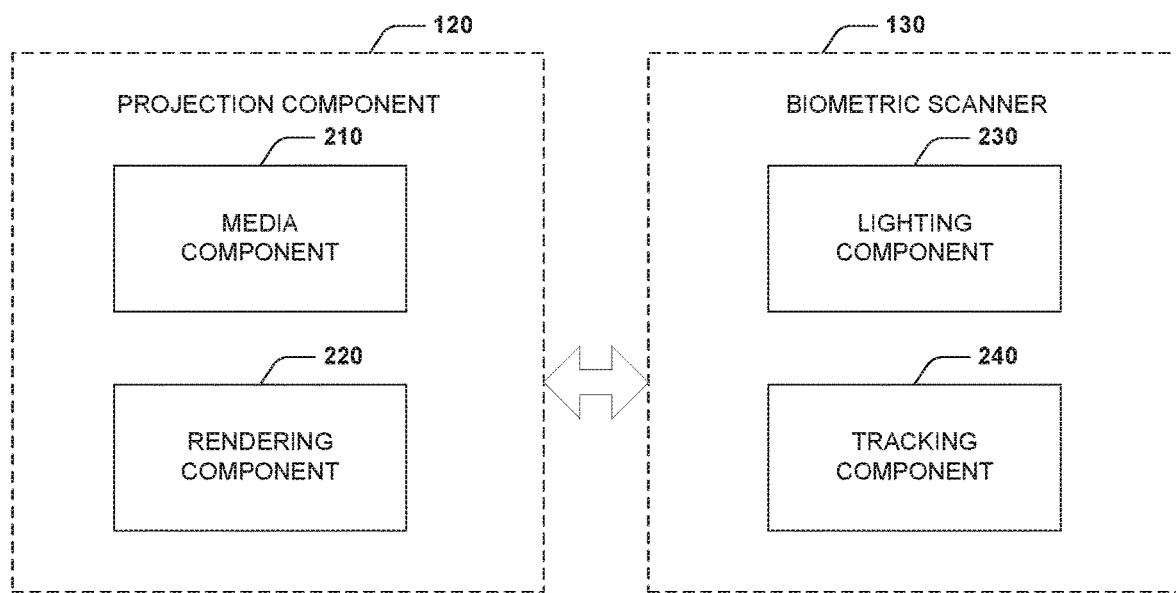
FIG. 2 illustrates an example component diagram of a projection component and a biometric scanner.

FIG. 2 illustrates a detailed example component diagram of a projection component 120 and biometric scanner 130. In some embodiments, the projection component 120 and the biometric scanner 130 are separate components that operate in tandem with the system 100 and/or processors. In other embodiments, the projection component 120 and the biometric scanner 130 are combined into an integrated device to leverage redundant hardware components. The projection component 120 includes a media component 210. The media component 210 receives the authentication image from the image database 110. The media component 210 can provide the authentication image such that the authentication image is projected onto the user and/or body part of the user when the user positions the body part in front (upon or in proximity) of the projection component 120.

The projection component 120 includes a rendering component 220. The rendering component 220 can track a user and/or body part of the user when in proximity of the projection component 120. In aspects, the rendering component 220 can determine the distance the body part of the user from the projection component 120. The rendering component 220 uses the distance to focus the authentication image onto the body part of the user by the projection component 120. In some embodiments, the rendering component 220 uses real time or near-real time adaptive focus to reproduce the authentication image onto the body part of the user with clarity.

The biometric scanner 130 includes a lighting component 230. The lighting component 230 can illuminate the user and/or body part of the user when in proximity of the biometric scanner 130. In some embodiments, the lighting component 230 provides infrared light such that blood vessel location can be tracked. In other embodiments, the lighting component 230 can read electrical signals in blood to determine blood vessel locations.

The biometric scanner 130 includes a tracking component 230. The tracking component 230 can track the blood vessel location in relation to the authentication image projected onto the user. In some embodiments, the tracking component 230 can capture an image of the body part of the user with the authentication image and the illuminated blood vessel. In other embodiments, the tracking component 230 can capture location coordinates of the blood vessel, the authentication image, and/or start and end points in the authentication image. In some embodiments, the tracking component 230 can read blood flow direction for further tracking and/or authentication steps.

Figure 3:
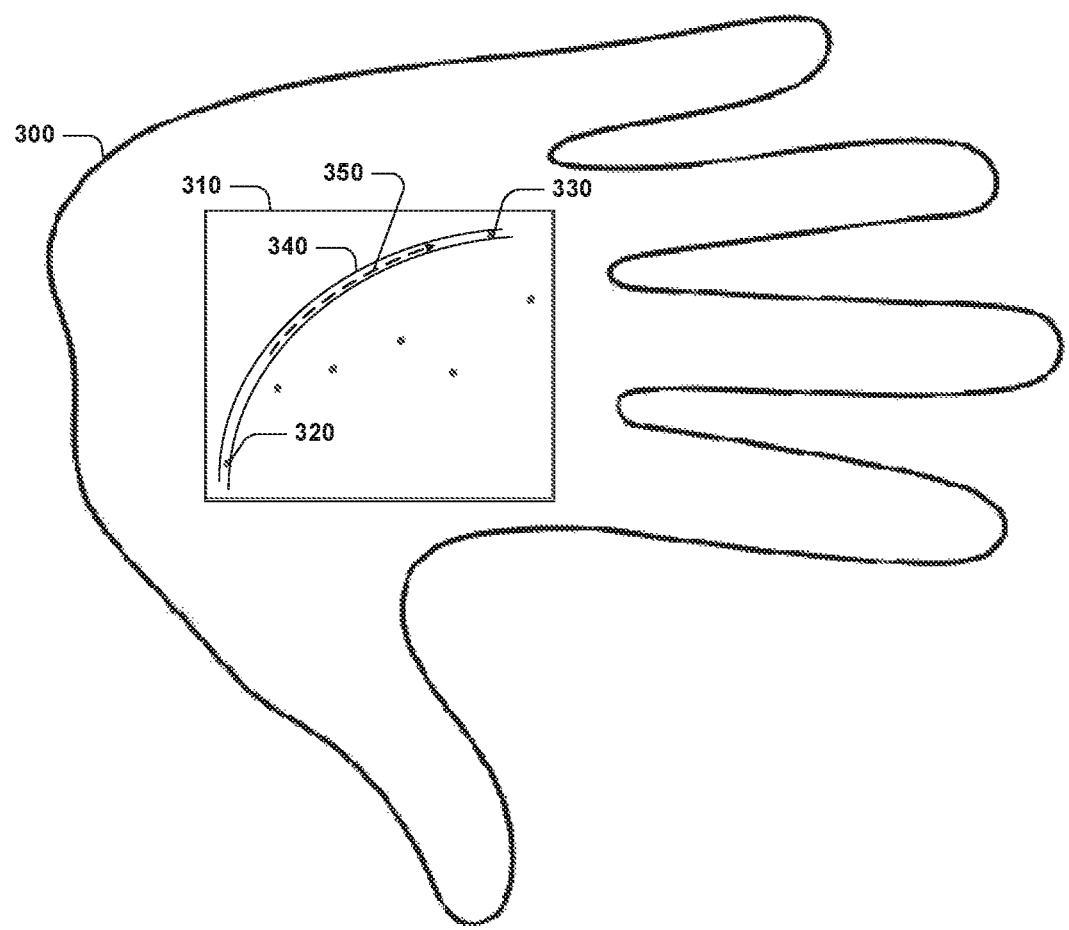
FIG. 3 illustrates an example projected authentication image and illuminated blood vessel.

FIG. 3, with continuing reference to FIG. 2, illustrates a detailed view of an example body part of the user 300 when operating the projection component 120 and the biometric scanner 130. For purposes of the example, the body part of the user is depicted as a hand. However, it is appreciated that most any body part or area of skin of the user may be chosen and operated with the system.

The projection component 120 via the rendering component 220 renders an authentication image 310 onto the body part of the user 300. For this specific example, the authentication image 310 depicted is a star constellation, e.g., the Big Dipper. It is appreciated that almost any image may be utilized.

The authentication image 310 includes a start point 320 and an end point 330. The start point 320 and end point 330 may be any body part or pixel of the authentication image. In some embodiments, the start point 320 and end point 330 are relatively easily identifiable, or notable, parts of the authentication image known only to the user. In this example, the start point 320 is the first star in the Big Dipper constellation and the end point is the last star in the Big Dipper constellation. In some embodiments, the user has previously selected a unique start point 320 and end point 330 such that they are specific to the user. In yet other embodiments, the user has been assigned a start point 320 and end point 330 by the system 100.

The biometric scanner 130 illuminates a blood vessel 340 on the body part of the user 300 via the lighting component 230. In some embodiments, the blood vessel 340 can be visible to the user such that the user can orient the blood vessel 340 to correspond to the start point 320 and end point 330. In other embodiments, the blood vessel 340 must track a distinct path, e.g. multiple points, traversing from the start point to the end point.

In yet other aspects, the comparison of blood vessel data and the authentication image can be processed. In other words, once the registration of a user's unique blood vessel data is associated to a unique image, authentication can be processed by reading the blood vessel data, e.g., via the biometric scanner 130. In this example, physical orientation of the blood vessel data with an authentication image need not be completed. Rather, the mapped data can be compared to data stored at registration thereby approving or otherwise denying authentication.

In other embodiments, the blood vessel 340 is displayed to the user on a display showing the authentication image 310 for orientation. In yet other embodiments, the biometric scanner 130 can reveal blood flow direction 350 within the blood vessel 340 such that the user can orient the body part 300 to the correct blood flow direction 350. The tracking component 240 can determine location data of the blood vessel 340 and the location data of the authentication image 310 and the start point 320 and end point 330. The authentication component 140 can receive the location data from the tracking component 240. The authentication component 140 authenticates the user upon determining blood in the blood vessel flows in the correct orientation from the start point 320 to the end point 330 in the authentication image 310.

Figure 4:
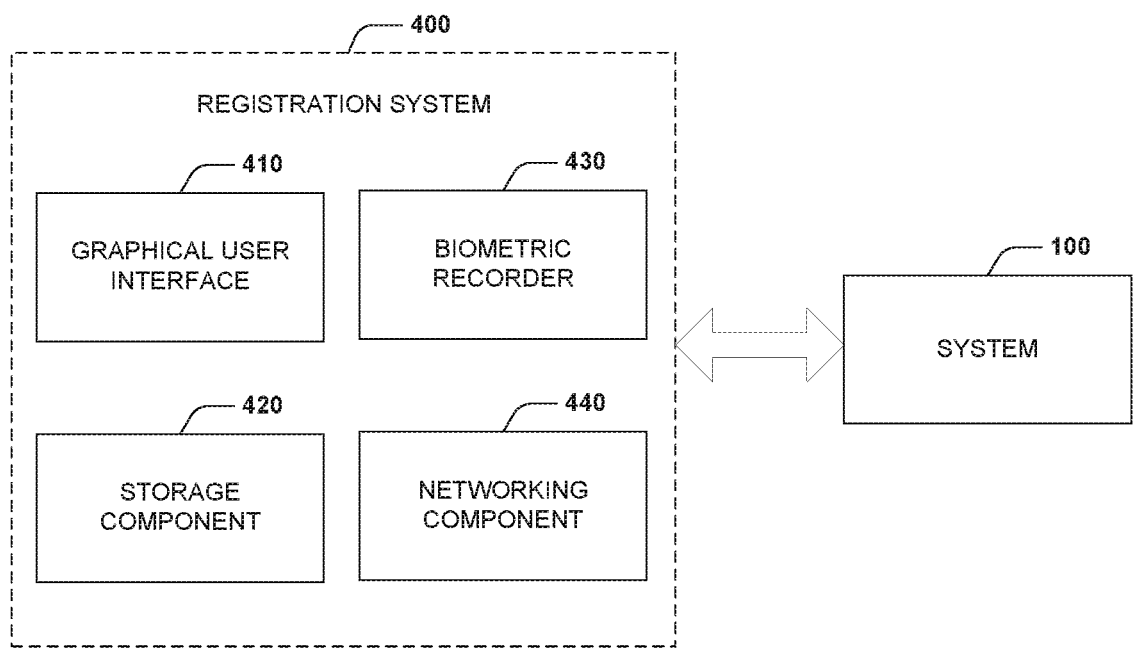
FIG. 4 illustrates an example component diagram of a registration system.

FIG. 4 illustrates a registration system 400. The registration system 400 initiates a user for future authentications. In this example, the registration system 400 can capture original user data that serves as the template for which a user matches to during future authentications. The registration system 400 includes a graphical user interface (GUI) 410. The GUI 410 provides a display and interface with which a user may make initial selections for future authentications. A user can initiate a registration via the GUI 410. In some embodiments, the user may select an authentication image via the GUI 410. In other embodiments, the user may upload or provide an authentication image to the registration system 400. The authentication image can be stored by the registration system 400 in a storage component 420. The GUI 410 can receive a selection of a start point and an end point within the authentication image. In some embodiments, the GUI 410 can receive a selection of a body part of the user that the user desires to use for authentication.

In yet other aspects, the system can suggest authentication images based upon a number of factors including, but not limited to, vein characteristics, account variables (e.g., value, balance amount), location, and/or the like. For instance, an image can be selected or suggested thereby alleviating a user selection and potentially addressing other security threshold considerations (e.g., more or less complex).

The storage component 420 can create a user profile to associate initial data about the user with the user profile. The storage component 420 can store the authentication image and start and end points as authentication data associated with the user profile. In some embodiments, the storage component 420 can store other user data such as social security number, financial account numbers, balances, routing numbers, and/or the like.

The registration system 400 includes a biometric recorder 430. The biometric recorder 430 collects biometric data about the user. The biometric recorder 430 can collect data about the blood vessel of a user. The biometric recorder 430 can record the pattern and/or unique location of blood vessel(s) in the body part of the user. The biometric recorder 430 can read blood vessel patterns, blood flow direction, blood vessel diameter, blood vessel dilation, blood vessel location, and/or the like. In some embodiments, the biometric recorder 430 reads the blood vessel data in association with the authentication image that is projected on the designated area of (or for) the user. The storage component 420 can store the specific orientation of the blood vessel in relation to the authentication image and the start and end points. The specific orientation can be used for future authentication of the user.

The registration component 400 includes a networking component 440. The networking component 440 can communicate with remote system(s) 100. The registration component 400 can provide user data to a system 100 when an authentication of a user is triggered or requested. The networking component 440 can provide the user data over a local area network (LAN), wireless LAN, or other networking protocols.

Figure 5:
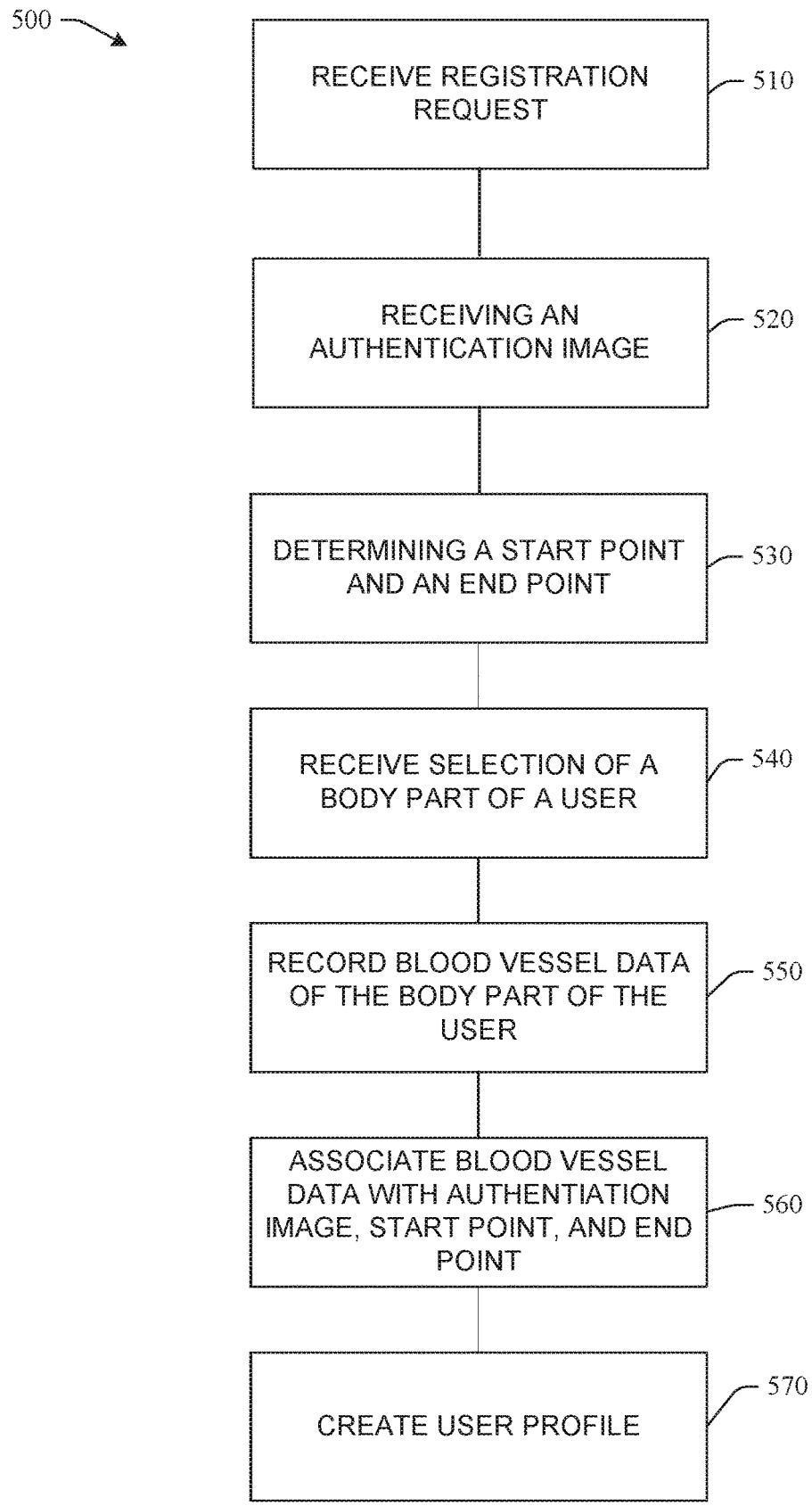
FIG. 5 illustrates an example method for registering a user for blood vessel image authentication in accordance with the innovation.
Figure 6:
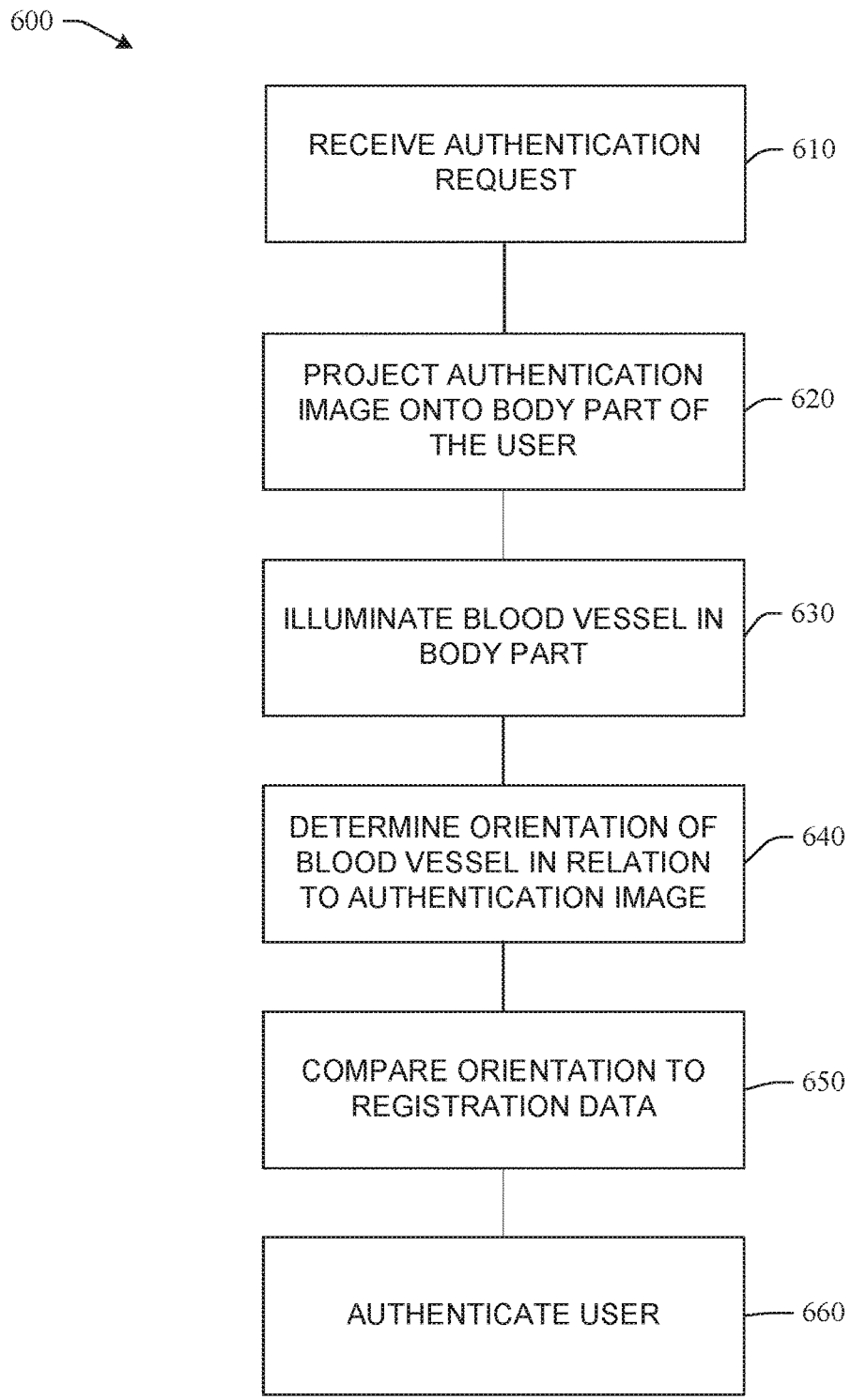
FIG. 6 illustrates an example method for blood vessel image authentication in accordance with the innovation.

With reference to FIG. 5 and FIG. 6, example methods 500 and 600 are depicted for authenticating a user to verify identity. While, for purposes of simplicity of explanation, the one or more methodologies shown herein, e.g., in the form of a flow chart, are shown and described as a series of acts, it is to be understood and appreciated that the subject innovation is not limited by the order of acts, as some acts may, in accordance with the innovation, occur in a different order and/or concurrently with other acts from that shown and described herein. For example, those skilled in the art will understand and appreciate that a methodology could alternatively be represented as a series of interrelated states or events, such as in a state diagram. Moreover, not all illustrated acts may be required to implement a methodology in accordance with the innovation. It is also appreciated that the method 500 and 600 are described in conjunction with a specific example is for explanation purposes.

FIG. 5 illustrates a method 500 for registering a user for future authentication. The method 500 can begin at 510 by receiving a registration request. For example, a user is to be registered to use blood vessel image authentication when completing future financial transactions. At 520, an authentication image is received. For example, the user that is being registered may provide an image to be used, or select from a number of stock images provided by a registration system. At 530, a start point and an end point are determined. Continuing the example, the user may select a distinct start point and end point within the authentication image. In some embodiments, the user may be assigned unique start and end points by the registration system. In other embodiments, the authentication image has standardized start and end points.

At 540, a selection of a body part of the user is received. In the example, the user can choose the back of a hand, a palm, a forearm, or most any other body part and/or portion of skin to present at authentication. In some embodiments, the body part is standardized to a specific body part and/or area of skin. At 550, blood vessel data is recorded of the body part of the user. The blood vessel data can include blood vessel patterns, blood flow direction, blood vessel diameter, blood vessel dilation, blood vessel location, and/or the like.

At 560, the blood vessel data is associated with the authentication image, the start point, and the end point in the authentication image. In the example, blood vessel location data is associated with the authentication image such that the blood vessel appears to connect the start point to the end point in the authentication image when the authentication image is overlaid, e.g., projected onto the blood vessel of the body part of the user. At 570, a user profile is created to store the association and the recorded data of the user. Further user data may be associated with the user profile such as financial accounts and/or the like.

FIG. 6 illustrates a method 600 for authenticating a user to confirm the user's identity. In aspects, method 600 can begin at 610 by receiving an authentication request. For example, a user desires to complete a financial transaction such as an ATM withdrawal. The user and/or the financial institution may initiate an authentication request to authenticate the user. In some embodiments, the user may be presented with multiple images from which to select, including the authentication image. The user must select the authentication image that is associated with the user account in order to proceed with further authentication steps.

At 620, the authentication image is projected onto the body part of the user. In the example, the user orients the body part in front of a projector component such that the authentication image can be projected onto the body part. The start point and end point within the authentication image are not indicated in the authentication image. Therefore, only the user knows where the start point and end point are located within the authentication image.

At 630, blood vessels in the body part are illuminated. In the example, the same area of the body part where the authentication image is projected is illuminated such that the underlying blood vessel(s) are shown with the authentication image. At 640, the orientation of the blood vessel in relation to the authentication image is determined. At 650, the orientation is compared to registration data. For example, the blood vessel can appear to connect the start point and the end point in the authentication image.

If the orientation matches the registration orientation the user provided previously, the user is authenticated at 660. If the orientation does not match, the user is denied authentication and cannot proceed with a transaction. As described above, exactness of the match (and subsequent authentication) can be user-defined, entity-defined or the like. Similarly, exactness can be based upon most any factors including but not limited to history, transaction type, transaction amount, user identity, account owner, etc.

Figure 7:
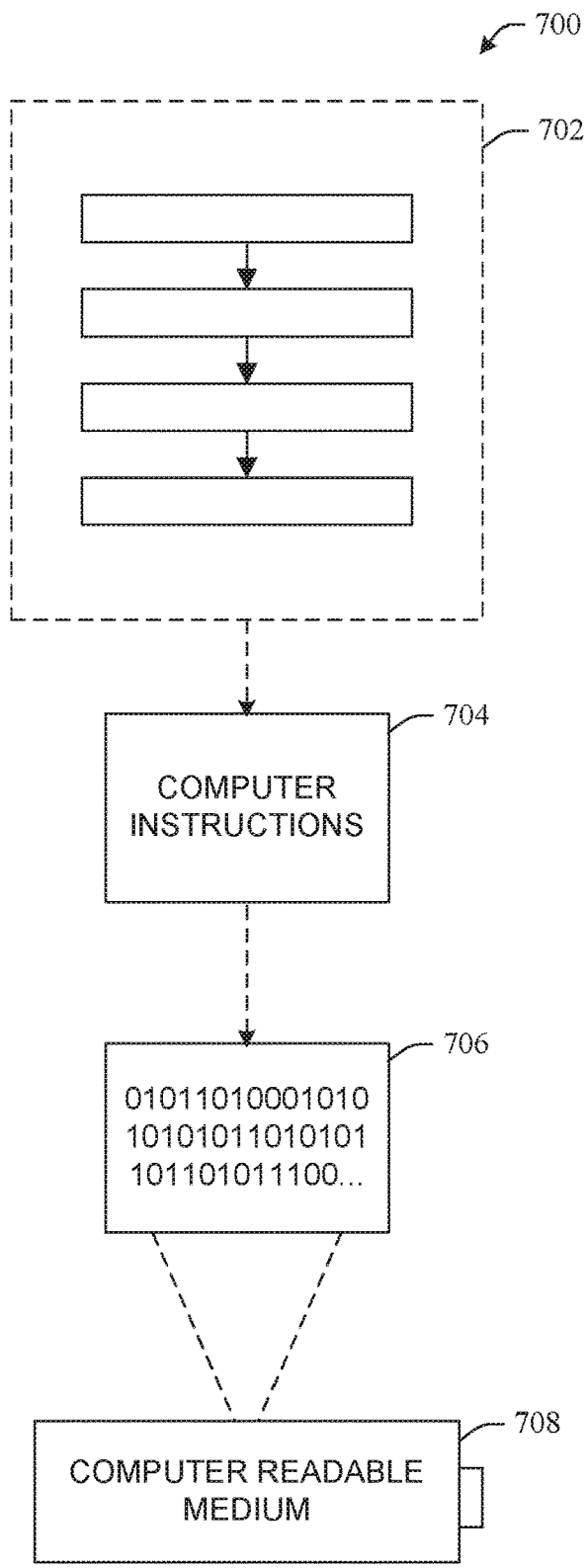
FIG. 7 illustrates a computer-readable medium or computer-readable device comprising processor-executable instructions configured to embody one or more of the provisions set forth herein, according to some embodiments.

Still another embodiment can involve a computer-readable medium comprising processor-executable instructions configured to implement one or more embodiments of the techniques presented herein. An embodiment of a computer-readable medium or a computer-readable device that is devised in these ways is illustrated in FIG. 7, wherein an implementation 700 comprises a computer-readable medium 708, such as a CD-R, DVD-R, flash drive, a platter of a hard disk drive, etc., on which is encoded computer-readable data 706. This computer-readable data 706, such as binary data comprising a plurality of zero's and one's as shown in 706, in turn comprises a set of computer instructions 704 configured to operate according to one or more of the principles set forth herein. In one such embodiment 700, the processor-executable computer instructions 704 is configured to perform a method 702, such as at least a portion of one or more of the methods described in connection with embodiments disclosed herein. In another embodiment, the processor-executable instructions 704 are configured to implement a system, such as at least a portion of one or more of the systems described in connection with embodiments disclosed herein. Many such computer-readable media can be devised by those of ordinary skill in the art that are configured to operate in accordance with the techniques presented herein.

Figure 8:
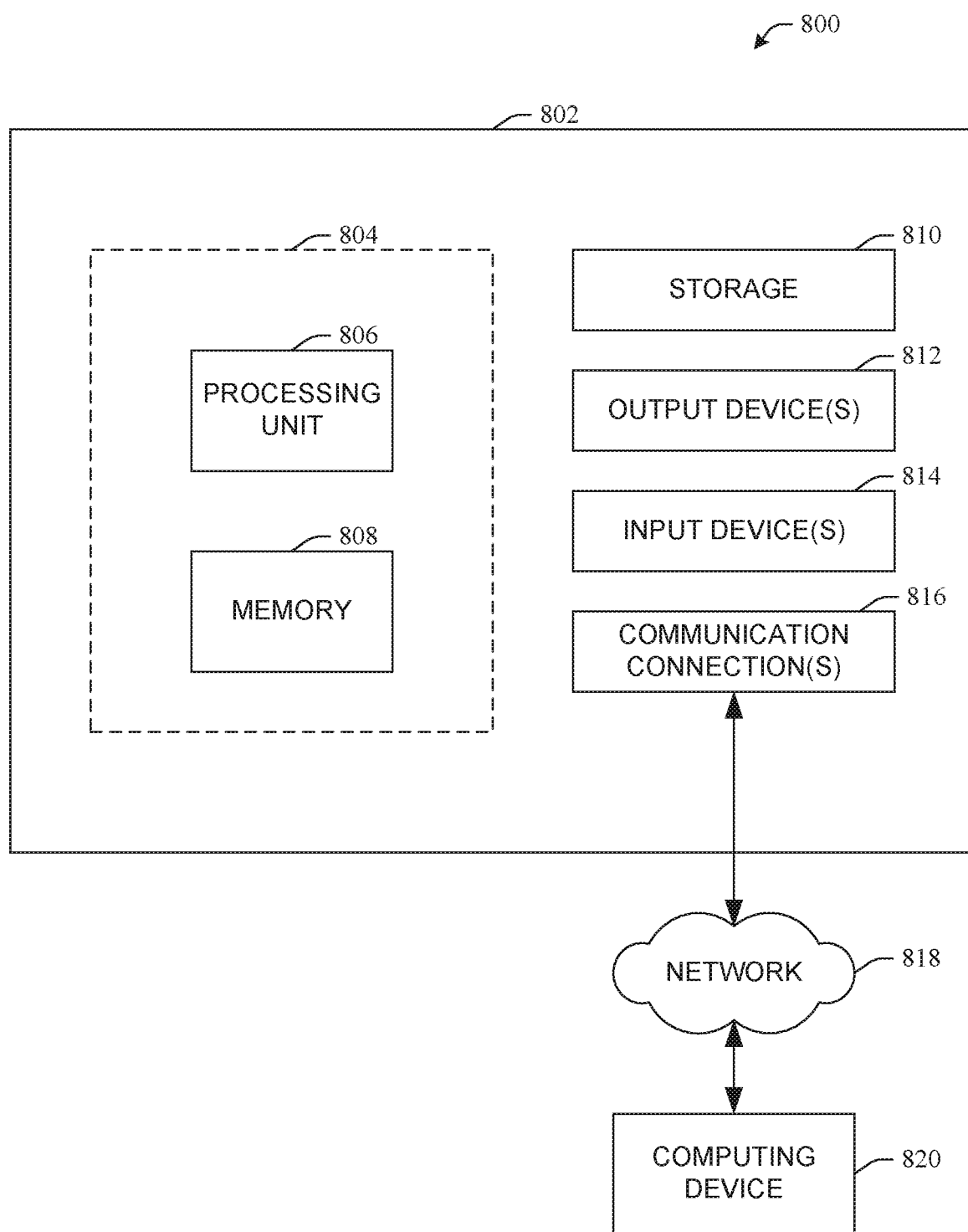
FIG. 8 illustrates a computing environment where one or more of the provisions set forth herein can be implemented, according to some embodiments.

With reference to FIG. 8 and the following discussion provide a description of a suitable computing environment in which embodiments of one or more of the provisions set forth herein can be implemented. The operating environment of FIG. 8 is only one example of a suitable operating environment and is not intended to suggest any limitation as to the scope of use or functionality of the operating environment. Example computing devices include, but are not limited to, personal computers, server computers, hand-held or laptop devices, mobile devices, such as mobile phones, Personal Digital Assistants (PDAs), media players, tablets, and the like, multiprocessor systems, consumer electronics, mini computers, mainframe computers, distributed computing environments that include any of the above systems or devices, and the like.

Generally, embodiments are described in the general context of "computer readable instructions" being executed by one or more computing devices. Computer readable instructions are distributed via computer readable media as will be discussed below. Computer readable instructions can be implemented as program modules, such as functions, objects, Application Programming Interfaces (APIs), data structures, and the like, that perform particular tasks or implement particular abstract data types. Typically, the functionality of the computer readable instructions can be combined or distributed as desired in various environments.

FIG. 8 illustrates a system 800 comprising a computing device 802 configured to implement one or more embodiments provided herein. In one configuration, computing device 802 can include at least one processing unit 806 and memory 808. Depending on the exact configuration and type of computing device, memory 808 may be volatile, such as RAM, non-volatile, such as ROM, flash memory, etc., or some combination of the two. This configuration is illustrated in FIG. 8 by dashed line 804.

In these or other embodiments, device 802 can include additional features or functionality. For example, device 802 can also include additional storage such as removable storage or non-removable storage, including, but not limited to, magnetic storage, optical storage, and the like. Such additional storage is illustrated in FIG. 8 by storage 810. In some embodiments, computer readable instructions to implement one or more embodiments provided herein are in storage 810. Storage 810 can also store other computer readable instructions to implement an operating system, an application program, and the like. Computer readable instructions can be accessed in memory 808 for execution by processing unit 806, for example.

The term "computer readable media" as used herein includes computer storage media. Computer storage media includes volatile and nonvolatile, non-transitory, removable and non-removable media implemented in any method or technology for storage of information such as computer readable instructions or other data. Memory 808 and storage 810 are examples of computer storage media. Computer storage media includes, but is not limited to, RAM, ROM, EEPROM, flash memory or other memory technology, CD-ROM, Digital Versatile Disks (DVDs) or other optical storage, magnetic cassettes, magnetic tape, magnetic disk storage or other magnetic storage devices, or any other medium which can be used to store the desired information and which can be accessed by device 802. Any such computer storage media can be part of device 802.

The term "computer readable media" includes communication media. Communication media typically embodies computer readable instructions or other data in a "modulated data signal" such as a carrier wave or other transport mechanism and includes any information delivery media. The term "modulated data signal" includes a signal that has one or more of its characteristics set or changed in such a manner as to encode information in the signal.

Device 802 can include one or more input devices 814 such as keyboard, mouse, pen, voice input device, touch input device, infrared cameras, video input devices, or any other input device. One or more output devices 812 such as one or more displays, speakers, printers, or any other output device can also be included in device 802. The one or more input devices 814 and/or one or more output devices 812 can be connected to device 802 via a wired connection, wireless connection, or any combination thereof. In some embodiments, one or more input devices or output devices from another computing device can be used as input device(s) 814 or output device(s) 812 for computing device 802. Device 802 can also include one or more communication connections 816 that can facilitate communications with one or more other devices 820 by means of a communications network 818, which can be wired, wireless, or any combination thereof, and can include ad hoc networks, intranets, the Internet, or substantially any other communications network that can allow device 802 to communicate with at least one other computing device 820.

What has been described above includes examples of the innovation. It is, of course, not possible to describe every conceivable combination of components or methodologies for purposes of describing the subject innovation, but one of ordinary skill in the art may recognize that many further combinations and permutations of the innovation are possible. Accordingly, the innovation is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A system, comprising:
a processor coupled to a memory that includes instructions that when executed by the processor cause the processor to:
trigger projection of an authentication image associated with a user on a body part of the user, wherein the authentication image comprises a first predetermined point and a second predetermined point;
read blood vessel data from the body part of the user on which the authentication image is projected;
determine whether a blood vessel is aligned with the authentication image such that the blood vessel appears to connect the first predetermined point to the second predetermined point; and
authenticate the user when the blood vessel is aligned.

2. The system of claim 1, wherein the instructions further cause the processor to:
provide a set of images to the user, the set of images including the authentication image and at least one other image; and
receive a selection of the authentication image.

3. The system of claim 1, wherein the blood vessel data includes at least one of a blood vessel position, a blood flow direction, a pulse, or a vital sign.

4. The system of claim 3, wherein the instructions further cause the processor to:
determine the blood flow direction from the first predetermined point to the second predetermined point; and
determine whether the blood vessel is aligned base on comparison of the blood flow direction to a predetermined blood flow direction.

5. The system of claim 1, wherein the authentication image comprises one or more additional predetermined points; and wherein the instructions further cause the processor to:
determine whether the blood vessel is aligned based on whether the blood vessel appears to connect the one or more additional predetermined points.

6. The system of claim 1, wherein the instructions further cause the processor to:
determine a measure of precision of the alignment of the blood vessel with the authentication image;
compare the measure of precision to a predetermined threshold; and
determine whether the blood vessel is aligned with the authentication image based on a result of the comparison.

7. The system of claim 6, wherein the predetermined threshold is based on one of user risk tolerance, data sensitivity, or transaction amount.

8. The system of claim 1, wherein the authentication image is predetermined and associated with previously recorded blood vessel data.

9. The system of claim 1, wherein the body part of the user is an area of the user selected during registration.

10. A method, comprising:
executing on a processor, instructions that cause the processor to perform operations comprising:
triggering projection of an authentication image associated with a user on a body part of the user, wherein the authentication image comprises a first predetermined point and a second predetermined point;
reading blood vessel data from the body part of the user on which the authentication image is projected;
determining whether a blood vessel is aligned with the authentication image such that the blood vessel appears to connect the first predetermined point to the second predetermined point; and
authenticate the user when the blood vessel is aligned.

11. The method of claim 10, the operations further comprising:
providing a set of images to the user, the set of images including the authentication image and at least one other image; and
receive a selection of the authentication image.

12. The method of claim 10, the operations further comprising determining blood flow direction in the blood vessel.

13. The method of claim 12, wherein determining whether the blood vessel is aligned further comprises:
determining the blood flow direction from the first predetermined point to the second predetermined point.

14. The method of claim 10, the operations further comprising:
determining a plurality of intermediary points in the authentication image based on a registration blood vessel image connecting the first predetermined point and the second predetermined point; and
wherein determining whether the blood vessel is aligned further comprises determining the blood vessel connects the first predetermined point, the second predetermined point, and at least a subset of the plurality of intermediary points.

15. The method of claim 10, the operations further comprising:
determining a measure of precision of the alignment of the blood vessel with the authentication image;
comparing the measure of precision to a predetermined threshold; and
determining whether the blood vessel is aligned with the authentication image based on a result of the comparing.

16. An authentication method, comprising:
presenting a first image of a set of blood vessels of a body part of a user on the body part;
projecting a second image associated with the user on the body part of the user over the first image, wherein the second image comprises a first predetermined point and a second predetermined point;
determining whether the second image is aligned with the first image such that a blood vessel of the set of blood vessels in the first image appears to connect the first predetermined point to the second predetermined point; and
authenticating a user when the second image is aligned with the first image.

17. The method of claim 16, further comprising: determining a pulse prior to projecting the second image.

18. The method of claim 16, further comprising:
determining distance between a projector of the second image and the body part; and
automatically focusing the second image based on the distance.

19. The method of claim 16, further comprising:
presenting a set of images including the second image and at least one other image; and
receiving a selection of the second image.

20. The method of claim 16, further comprising:
determining a measure of precision of the alignment of the second image with the first image;
comparing the measure of precision to a predetermined threshold; and
determining whether the second image is aligned with the first image based on a result of the comparing.

\* \* \* \* \*